United States Patent [19]

Cavazza

[11] 4,362,719

[45] Dec. 7, 1982

[54] THERAPEUTIC METHOD AND COMPOSITIONS FOR THE TREATMENT OF JUVENILE DIABETES MELLITUS

[76] Inventor: Claudio Cavazza, 35, Via Marocco, Rome, Italy, 00144

[21] Appl. No.: 264,044

[22] Filed: May 15, 1981

[30] Foreign Application Priority Data

May 15, 1980 [IT] Italy .............................. 48692 A/80

[51] Int. Cl.³ .................... A61K 31/26; A61K 31/205
[52] U.S. Cl. ..................................... 424/178; 424/316
[58] Field of Search ................................ 424/316, 178

[56] References Cited

PUBLICATIONS

Chem. Abst., vol. 93, Chem-Sub. Index, p. 5189CS, 12-31-80.
Chem. Abst., vol. 93, 129356v, (1980).

Primary Examiner—Stanley J. Friedman
Attorney, Agent, or Firm—Bruce M. Collins

[57] ABSTRACT

The oral or parenteral administration of L-carnitine or certain acyl L-carnitines, typically propionyl L-carnitine, or the pharmacologically acceptable salts thereof, permits a considerable reduction (from 20 to approximately 50%) of the daily dose of insulin required by patients having juvenile diabetes mellitus to restore normal blood glucose levels.

Moreover, L-carnitine and such acyl carnitines actively inhibit ketoacidosis, thus avoiding the risk of ketoacidosic coma in such patients.

4 Claims, 1 Drawing Figure

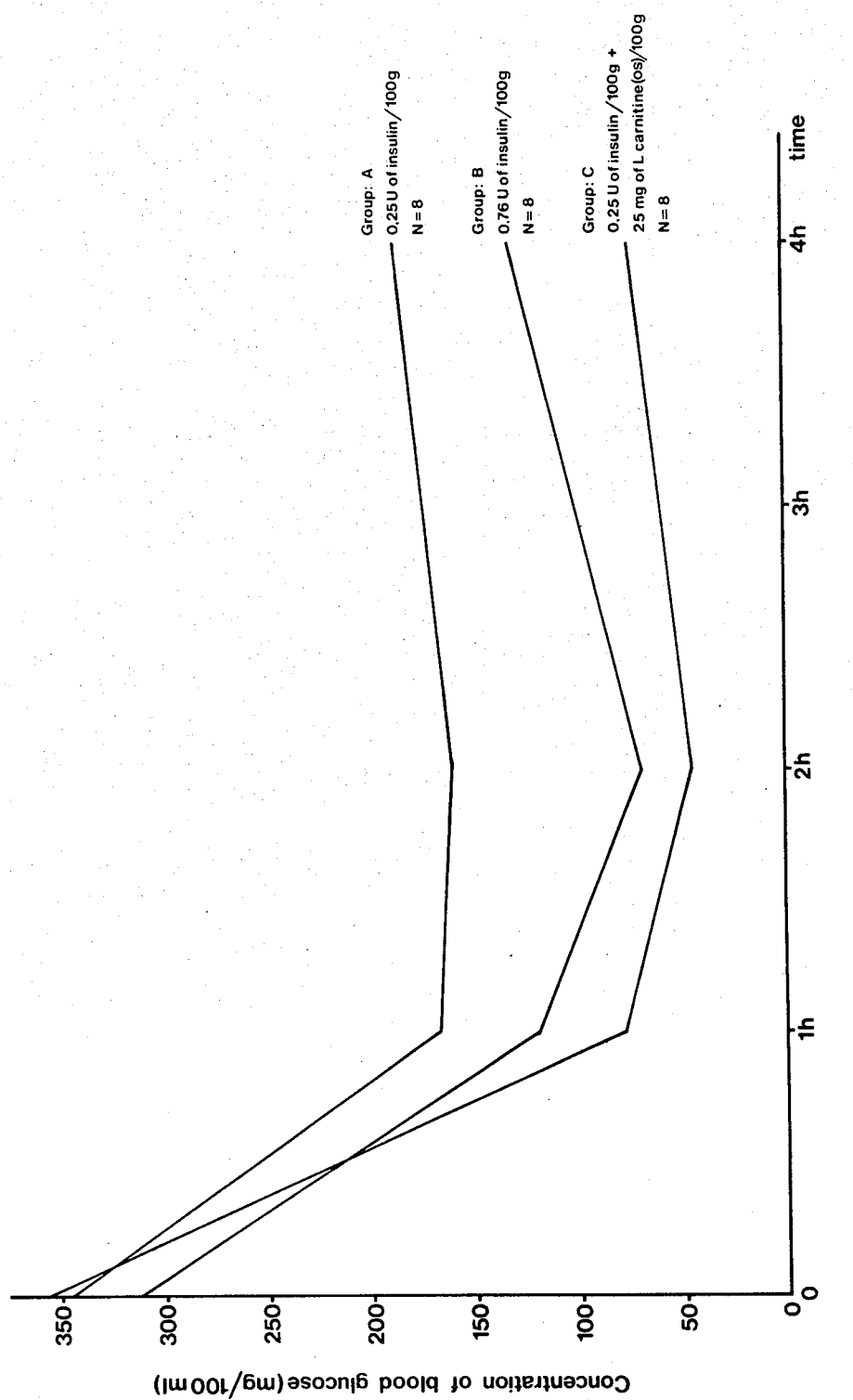

THERAPEUTIC METHOD AND COMPOSITIONS FOR THE TREATMENT OF JUVENILE DIABETES MELLITUS

The present invention pertains to a therapeutic method for the treatment of patients having juvenile diabetes mellitus and to a pharmaceutical composition for use in such a method.

According to the severity of the insufficiency in insulin secretion, a subject having diabetes mellitus may fall within one of two classes: those prone to ketoacidosis and those who are not. The subject prone to ketoacidosis is a diabetic affected by juvenile diabetes mellitus (generally diabetes with onset before 25 years of age approx.) and to avoid ketoacidosis is insulin-dependent throughout life. This diabetic condition is the most severe, and the patient's life and social and occupational activities are seriously conditioned by the disease. Besides totally depending on daily insulin administration, the patient must constantly be on guard against two events representing the two extremes resulting from insufficient insulin secretion: ketoacidosic coma (requiring immediate insulin administration) and insulin shock (hypoglycaemia) provoked by an overdose of insulin. In addition to the patient himself, persons who are in close contact with him, also must be trained to quickly recognise the premonitory symptoms of the above-described events and to dispense appropriate and immediate treatment, particularly in the case of hypoglycaemia.

It is likewise known that the various drugs administerable via the oral route (sulfonylurea compounds, tolbutamide, chlorpropamide, acetohexamide and tolazamide; biguanides; phenformin) developed over the last decade for treating some mild forms of diabetes (since their efficacy is in fact circumscribed to the treatment of a limited number of selected patients) can not be employed as a substitute for insulin in the patient prone to ketoacidosis. Although the mechanisms of action of such drugs have not yet been fully elucidated, it is known that such drugs are not oral substitutes for insulin. Moreover, the impossibility of accurately measuring the biological half-life following oral administration makes the choice of the dose and administration intervals difficult and to some extent fortuitous.

It would thus be highly desirable to find a substance which would permit a reduction in the required dosage of insulin in patients having juvenile diabetes mellitus and prone to ketoacidosis. Ideally such a substance would be effective when administered orally.

The increasing world problem of insulin supplies, largely due to the persistent incapability of synthetically producing this essential hormone on an industrial scale, and the advantage which would derive from the possibility of reducing the daily dosage of insulin with relative decrease in the frequency of insulin injections and reduced risk of hypoglycaemic shock are only some of the reasons that show the importance of having available such substitute substance.

Research directed at locating an insulin substitute has concentrated primarily on inhibitors of fatty acid oxidation [see Muntoni et al., Advances in Lipid Research, 12, 311–377 (1974), Academic Press] and this is one proposed mechanism of action of such agents as the biguanides. In fact, the carnitine-dependent fatty acid transport system has been suggested as the target of the biguanides action (ibid) which in turn has prompted the theory that analogs of carnitine which antagonize or inhibit the role of carnitine in the fatty acid transport system might be effective antidiabetic agents. Previous studies have suggested that carnitine has no effect on glycoregulation and does not alter the daily insulin requirements—Bekaert et al., Clin. Chim. 5, 177–180 (1960). While the ester carnitine carnitate did reduce the daily insulin requirement [see Bekaert et al., Ann. Endcr. 18, 218–229 (1957)], this effect was a consequence of the parasympathomimetic action of carnitine carnitate, a property not demonstrated by carnitine. See Strack et al., Acta biol. med. germ., 35, 645–656 (1976).

In consideration of the foregoing, it is surprising and unexpected that precisely L-carnitine and certain acyl derivatives thereof, i.e. the compounds represented by the general formula:

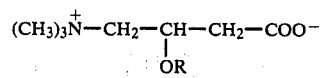

wherein R is acetyl, propionyl, butyryl or hydroxybutyryl and the pharmacologically acceptable salts thereof, administerable either via the parenteral or oral route, can replace from approximately 20 to 50% of the daily insulin dose that otherwise would be necessary to achieve an identical glucose lowering effect in the absence of L-carnitine or the aforementioned acyl L-carnitines. Moreover the foregoing compounds have been shown to be powerful inhibitors of ketoacidosis. L-carnitine and all such acyl L-carnitines are in fact known for being powerful activators of fatty acid oxidation. In contrast to the sulfonylurea compounds and the biguanides, L-carnitine and the aforementioned acyl L-carnitines and the pharmacologically acceptable salts thereof are an effective insulin substitute for the treatment of insulin-dependent patients having juvenile diabetes mellitus and prone to ketoacidosis.

Therefore, the following subject matters fall within the scope of the present invention:

(a) L-carnitine and L-acylcarnitine having general formula:

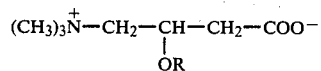

wherein R is acetyl, propionyl, butyryl or hydroxybutyryl and the pharmacologically acceptable salts thereof, as agents which partially replace insulin and inhibit ketoacidosis in the therapeutical treatment of insulin-dependent patients suffering from juvenile diabetes mellitus.

(b) An orally or parenterally administrable pharmaceutical composition for the therapeutical treatment of insulin-dependent patients suffering from juvenile diabetes mellitus, which comprises:

(1) an amount of L-carnitine or L-acyl carnitine having general formula:

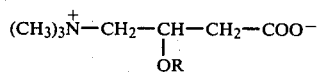

wherein R is acetyl, propionyl, butyryl or hydroxybutyryl and the pharmaceutical acceptable salts thereof, sufficient to replace a portion of the insulin dose which should be administered to said patients in order to restore glycemia thereof to normal value and inhibit ketoacidosis; and (2) a pharmacologically acceptable excipient.

(c) A therapeutical method for the treatment of insulin-dependent patients suffering from juvenile diabetes mellitus, which comprises the steps of:
(1) administering to said patients a reduced daily dose of insulin, lower by about 20–50% to the daily dose needed for restoring glycemia to normal value; and
(2) orally or parenterally administering to said patients a daily dose of L-carnitine or L-acyl carnitine having general formula:

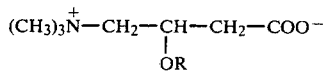

wherein R is acetyl, propionyl, butyryl or hydroxybutyryl or the pharmacologically acceptable salts thereof, sufficient in combination with said reduced dose of insulin, to restore glycemia to normal value and inhibit ketoacidosis.

Generally, a daily dose comprised between about 5 and about 50 mg of L-carnitine will be administered or an equivalent amount of acyl L-carnitine or a pharmacologically acceptable salt thereof per Kg of body weight.

Among the foregoing acyl L-carnitines, propionyl L-carnitine is particularly preferred.

A preferred embodiment of pharmaceutical composition in accordance with the invention is a liquid, subcutaneously injectable composition, which comprises per each ml of composition:
(a) from about 20 to about 30 U of insulin;
(b) from about 0.2 to about 1 g of L-carnitine or an equivalent amount of an acyl carnitine having general formula:

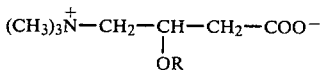

wherein R is acetyl, propionyl, butyryl, hydroxybutyryl or the pharmacologically acceptable salts thereof, and
(c) a pharmacologically acceptable liquid excipient.

A particularly preferred embodiment of pharmaceutical composition in accordance with the invention is a subcutaneously injectable, liquid composition which comprises per each ml of composition:
(a) from about 20 to about 30 U of slow-acting insulin;
(b) from about 0.1 from about 0.5 g of L-carnitine or an equivalent amount of a pharmacologically acceptable salt thereof;
(c) from about 0.1 to about 0.25 g of an acyl derivative of L-carnitine characterized by a biological half-life of about 6–12 hours; and
(d) from about 0.1 to about 0.25 g of an acyl derivative of L-carnitine characterized by a biological half-life of about 12–24 hours.

The effect of L-carnitine and acyl derivatives such as propionyl L-carnitine can be conveniently observed in laboratory models, as for example the streptozotocin diabetic rat (65 mg/kg i.p.). The results are illustrated in Tables I, II, III, IV and in the attached diagram. More specifically, in Table I are shown the variations of the blood glucose levels in consequence of administration of (a) saline solution, (b) insulin, (c) L-carnitine, and (d) insulin + L-carnitine.

In Table II the results are those obtained by substituting L-propionyl carnitine for L-carnitine. The results of these tests show that while L-carnitine and propionyl L-carnitine do not modify the glycaemia of diabetic rats, they nevertheless significantly enhance the hypoglycaemia-inducing action of insulin.

Table III illustrates the enhancing effect of L-carnitine toward the action of insulin in reducing the ketone bodies.

In the drawing there are shown the glycaemic curves concerning:

A, a first group of diabetic rats (group A) treated with an insulin dose (0.25 U/100 g) clearly insufficient to bring about a significant decrease in blood glucose;

B, a second group of diabetic rats (group B) treated with an insulin dose (0.76 U/100 g) sufficient to bring about a significant decrease in blood glucose; and C, a third group of diabetic rats (group C) treated with the same insufficient insulin dose as that of group A + 25 mg/kg of body weight of L-carnitine (per os).

The results show that the administration of L-carnitine enhances the hypoglycaemia-inducing action of insulin as far as exceeding the minimum value of glycaemia brought about by a dose of insulin alone three time as high.

In fact, the value of group C is statistically significant at 1% towards the value of group B at the times of 1 hour and 4 hours, and at 5% at the time of 2 hours, while the value of group B and C are constantly significant at 1% towards group A.

Moreover, the hypoglycaemia-inducing effect obtained in the presence of L-carnitine is longer lasting, as shown by the smaller angular coefficient of the plot for group C between the times of 2 hours and 4 hours, as compared with group B.

Table IV summarizes the results of a further experiment which was carried out in the following manner:

A first group of 13 streptozotocin-diabetic rats received L-carnitine, 250 mg/kg daily in single p.o. doses for 15 days.

A second group of 8 streptozotocin-diabetic rats did not receive L-carnitine. All the animals were free to eat and drink ad libitum.

Every day, weight gain, and food and water intake were checked. On the 16th day serum glucose, total ketone bodies and free carnitine were measured. The outcome along with the results obtained with a group of 5 healthy untreated rats having the same weight as the test animals are shown in table IV.

It is clearly apparent the remarkable effect of L-carnitine in lowering food and water intake (which streptozotocin treatment had previously increased), and in reducing glycaemia and ketonaemia, besides—as expected—in restoring carnitinaemia to normal.

TABLE I

Blood glucose (mg/100 ml) vs. administration of saline, insulin, L-carnitine and insuline + L-carnitine in streptozotocin (STZ) diabetic rats

| | 48 hours after STZ administration | days of treatment | | | | |
|---|---|---|---|---|---|---|
| | | 1 | 2 | 3 | 4 | |
| Saline | 317 ± 8 | 324 ± 14 | 332 ± 17 | 294 ± 9 | 321 ± 13 | n = 13 |
| L-carnitine (250 mg/kg p.o. × 2) | 306 ± 10 | 329 ± 12 | 308 ± 14 | 296 ± 15 | 275 ± 10 | n = 17 |
| Insulin (2U/100 g Lente ® Insulin s.c. × 2) | 312 ± 11 | 175 ± 23 | 135 ± 21 | 157 ± 12 | 143 ± 18 | n = 14 |
| L-carnitine (250 mg/kg p.o. × 2) + Insulin (2U/100 g s.c. × 2) | 302 ± 11 | 116 ± 19 | 99 ± 14 | 137 ± 14 | 118 ± 15 | n = 16 |

TABLE II

Blood glucose (mg/100 ml) vs. administration of saline, insulin, propionyl L-carnitine and L-propionyl carnitine + insulin in streptozotocin (STZ) diabetic rats.

| | 48 hours after STZ administration | days of treatment | | | | |
|---|---|---|---|---|---|---|
| | | 1 | 2 | 3 | 4 | |
| Saline | 317 ± 8 | 340 ± 12 | 322 ± 17 | 296 ± 9 | 299 ± 12 | n = 13 |
| L-propionyl carnitine (250 mg/kg p.o. × 2) | 306 ± 10 | 322 ± 14 | 298 ± 16 | 290 ± 16 | 270 ± 10 | n = 17 |
| Insulin (2U/100 g Lente ® Insulin s.c. × 2) | 312 ± 11 | 160 ± 24 | 128 ± 20 | 130 ± 11 | 145 ± 19 | n = 14 |
| L-propionyl carnitine (250 mg/kg p.o. × 2) + Insulin (2U/100 g s.c. × 2) | 302 ± 11 | 110 ± 18 | 89 ± 16 | 110 ± 12 | 120 ± 16 | n = 16 |

TABLE III

Acetoacetate, $\beta$-hydroxybutyrate ($\beta$-OH) and total serum ketone bodies (SKB) v.s. administration of saline, insulin, L-carnitine and insulin + L-carnitine in streptozotocin diabetic rats

| | Acetoacetate | $\beta$-OH | SKB |
|---|---|---|---|
| Saline | 83 ± 13 | 1371 ± 21 | 1454 ± 31 |
| L-carnitine (250 mg/kg p.o. × 2) | 68 ± 5 | 1353 ± 15 | 1422 ± 19 |
| Insulin (2U/100 g Lente ® Insulin s.c. × 2) | 40 ± 4 | 527 ± 10 | 567 ± 15 |
| Insulin (2U/100 g s.c. × 2) + L-carnitine (250 mg/kg p.o. × 2) | 21 ± 4* | 473 ± 8* | 494 ± 13* |

* = $P \leq 1\%$. N = 8 per group. The test animals were sacrificed and the measurements carried out on the fifth day after the treatment began.

TABLE IV

Effect of L-carnitine (250 mg/Kg per day, p.o.) on some physiological and biochemical parameters in streptozotocin-diabetic rats.

| | Streptozotocin diabetic rats | | Healthy rats |
|---|---|---|---|
| | L-carnitine UNTREATED RATS | L-carnitine TREATED RATS | control values |
| Body weight (g) | 230 ± 6 (8) | 239 ± 10 (13) | 357 ± 8 (5) |
| Water intake (ml/day/rat) | 168 ± 6 (8) | 126 ± 5*** (13) | 31.3 ± 0.6 (5) |
| Food intake (g/day/rat) | 38.8 ± 0.9 (13) | 34.7 ± 0.9*** (13) | 28.5 ± 0.5 (5) |
| Serum glucose (mg/dl) | 359 ± 19 (8) | 229 ± 23 (13) | 72.4 ± 3.2 (5) |
| Total ketone bodies ($\mu$M) | 747.6 ± 151.3 (8) | 416.6 ± 81.0* (13) | 73.0 ± 7.12 (5) |
| Free carnitine ($\mu$M) | 22.50 ± 1.10*** (8) | 49.19 ± 4.90** (13) | 35.05 ± 1.20 (5) |

Number of animals in brackets
*$p < 0.05$
**$p < 0.02$
***$p < 0.001$

Long term clinical trials have been conducted on a group of thirty diabetics between 22 and 63 years of age. These diabetics were subjected to a diet according to the traditional rules and suited to the specific conditions of age, weight, etc. The number of calories in the diet varied from 2,000 to 3,000 daily in accordance with the type of occupation.

Clinical examination, body-weight check, and urine analysis were carried out every two weeks for each patient and blood analysis was performed every 4–5 weeks. Glycaemia, cholesterol, total lipids and ketones were examined for each patient.

Prior to beginning the clinical tests, all the patients had been treated with insulin alone. The insulin doses were reduced and from 400 to 600 mg of L-carnitine were given orally daily.

In 70% of the cases, it was found that L-carnitine administration enabled the daily insulin intake to be reduced by approximately 21 to 52%.

Ketonaemia also remained within normal values in those cases which when previously on insulin therapy alone had periodically shown signs of ketoacidosis.

What is claimed is:

1. A sterile injectable pharmaceutical composition comprising:
   (a) insulin in a concentration of from about 20 to about 30 U/ml of composition;
   (b) at least one member selected from the group consisting of L-carnitine and the acetyl, propionyl, butyryl or hydroxybutyryl ester of L-carnitine in a concentration providing from about 0.2 to about 1 g/ml of composition; and (c) a pharmaceutically acceptable and injectable liquid carrier.

2. The sterile injectable pharmaceutical composition of claim 1 comprising (a) slow-acting insulin in a concentration of from about 20 to about 30 U/ml of composition;

(b) L-carnitine in a concentration providing from about 0.1 to about 0.5 g/ml of composition, or an equivalent amount of a pharmacologically acceptable salt thereof;

(c) a L-carnitine ester having a biological half-life of about 6–12 hours in a concentration providing from about 0.1 to about 0.25 g/ml of composition; and (d) a L-carnitine ester having a biological half-life of about 12–24 hours in a concentration providing from about 0.1 to about 0.25 g/ml of composition.

3. In the method of treating a human having juvenile diabetes mellitus with insulin, the improvement which comprises the administration to the human of a quantity of at least one member selected from the group consisting of L-carnitine and the acetyl, propionyl, butyryl and hydroxybutyryl ester thereof, at least sufficient to permit a significant reduction in the dosage of insulin otherwise required to maintain said human.

4. The method of claim 3, which comprises (a) administering to said human a daily dose of insulin reduced by about 20–50% of the daily dose otherwise required to maintain said human, and (b) orally or parenterally administering to said human a daily dose comprised between about 5 and about 50 mg of at least one member selected from the group consisting of L-carnitine and the acetyl, propionyl, butyryl or hydroxybutyryl thereof, per kg of body weight.

* * * * *